United States Patent [19]

Ibbotson

[11] Patent Number: 4,700,010

[45] Date of Patent: Oct. 13, 1987

[54] PROCESS FOR HYDROXYARYLALDEHYDES

[75] Inventor: Arthur Ibbotson, Glossop, United Kingdom

[73] Assignee: Imperial Chemical Industries PLC, London, England

[21] Appl. No.: 763,409

[22] Filed: Aug. 7, 1985

[30] Foreign Application Priority Data

Aug. 13, 1984 [GB] United Kingdom ................. 8420561

[51] Int. Cl.$^4$ ............................................. C07C 45/45
[52] U.S. Cl. ................................................... 568/433
[58] Field of Search ........................................ 568/433

[56] References Cited

U.S. PATENT DOCUMENTS 4,231,967 11/1980 Matsuda et al. .................... 568/433

FOREIGN PATENT DOCUMENTS 0106653 4/1984 European Pat. Off. ............ 568/433
1530248 10/1978 United Kingdom .

OTHER PUBLICATIONS

Tin (IV) Ethoxide-Catalysed Hydride Transfer from Alcohols to Carbonyl Compounds, by G. Casiraghi et al., J. C. S. Perkin II, pp. 407–411, 1980.
Selective Reactions Between Phenols and Formaldehyde, A Novel Route to Salicylaldehydes, by G. Casiraghi, et al., J. C. S. Perkin I, pp. 1862–1865, 1980.

Primary Examiner—Werren B. Lone
Attorney, Agent, or Firm—Cushman, Darby & Cushman

[57] ABSTRACT

A catalytic process for the formylation, in the 2-position, of optionally substituted phenols, particularly 4-nonylphenol, using a catalyst comprising a tin phenoxide and a tertiary amine.

9 Claims, No Drawings

PROCESS FOR HYDROXYARYLALDEHYDES

This invention relates to a process for the preparation of 2-hydroxyarylaldehydes.

These aldehydes and their derivatives are useful in many applications, e.g. in perfumes, pesticides, stabilising agents and as intermediates in the preparation of numerous compounds of industrial importance, including the oximes which are used in hydrometallurgical extraction processes. For this latter application it is desirable that the aldehyde is produced in a pure form free from dialdehydes. It is known from UK Patent No. 1530248 and JCS (Perkin I) 1980 p.1862 et seq. that a —CHO group may be selectively introduced into the 2-position relative to the —OH group of a phenol, by reacting formaldehyde with the phenol, in a aprotic solvent, in the presence of an amine and anhydrous tin chloride. In the latter reference it is postulated that the tin chloride reacts with phenol to produce a tin phenoxide which then acts as a catalyst for the introduction of the formyl group into the ring in a position adjacent to the OH group. The amine is believed to be required to absorb the HCl which is produced during the formation of the phenoxide and lesser or greater quantities of amine than are required for this purpose are shown to have an adverse effect on both yield and selectivity. It is also shown that strongly basic amines which can form stable complexes with tin phenoxide are less satisfactory for the reaction. Support for the mechanism is found in the reaction of formaldehyde with phenol in the presence of tin phenoxide itself although the yield is only reported as fair.

In another article by some of the authors of the above-mentioned article [JCS (Perkin II) 1980 P.407 et seq.] it is shown that the dehydrogenation of a 2-hydroxymethylphenol to the 2-formylphenol using a ketone or aldehyde as hydride acceptor and tin phenoxide as catalyst is adversely affected by the presence of amine. Furthermore dehydrogenation does not proceed if the aldehyde is aliphatic.

The process considered in the first references has a number of disadvantages particularly for operation on a commercial scale. The presence of formaldehyde and HCl or the amine hydrochloride salt and the by-product methanol in the same reaction mixture is expected to lead to the formation of chloromethyl ethers and methyl chloride which are carcinogenic. The yield and selectivity of the process also appear to depend upon the use of about 10 mole % of the tin chloride and up to 40 mole % of the amine based upon the phenol which would make commercial operation of the process very expensive and pose serious disposal problems for the effluent.

It has now been found that good selectivity for the formylation of phenols in the 2-position can be achieved in the absence of any carcinogenic by-products by the reaction of formaldehyde with the phenol in the presence of a tertiary amine and relatively low levels of an organoxy tin compound, provided the organoxy tin compound is such that, on extraction with water, the aqueous medium has a pH of from 6 to 10.

According to the present invention there is provided a process for the preparation of a 2-hydroxyarylaldehyde which comprises the reaction in an anhydrous medium of formaldehyde with a phenol, free from substituents in the 2-position, in the presence of a catalyst comprising (1) a tertiary amine and (2) a tin composition consisting of one or more compounds of the formula $Sn(OR)_4$, wherein R is an organic radical and wherein the tin composition is such that, on extraction with water, the resultant aqueous medium has a pH of from 6 to 10.

The phenol may be substituted in any or all positions, other than the 2-position, by groups which do not interfere with the course of the present process and which preferably are electron-repelling or weakly electron-attracting. Examples of suitable phenols include phenol itself, 4-alkylphenols such as 4-cresol and 4-t-butylphenol and 4-alkylphenols in which the alkyl group contains from 5 to 20 carbon atoms, and preferably from 7 to 12 carbon atoms, such as 4-nonylphenol.

The process of the present invention is especially suitable for the manufacture of 2-hydroxy-5-alkylbenzaldehydes which are intermediates in the manufacture of metal extractants based on 2-hydroxy-5-alkylbenzaldoximes. For example an isomeric mixture of 2-hydroxy-5-nonylbenzaldoximes may be prepared from 4-nonylphenol derived from phenol and propylene trimer, and consisting of an isomeric mixture containing straight and branched nonyl groups.

Both free gaseous formaldehyde, solutions of formaldehyde in anhydrous solvent and polymeric forms, such as paraformaldehyde and other conventional reagents which release formaldehyde may be used in the present process. Paraformaldehyde is found to be an especially convenient source of formaldehyde. If high conversion of the phenol is required the molar ratio of formaldehyde to phenol should be at least 2:1 and is preferably in the range 2 to 4:1, as two molecules of formaldehyde are required to introduce a single formyl group into the phenol ring, the second molecule being reduced to methanol. If, however, the process is used in the preparation of 2-hydroxyarylaldehydes which will be further converted into oximes for use in hydrometallurgical extraction, it is not always necessary to consume all the phenol because the oximes may be used in admixture with the free phenol. For such end use the ratio of formaldehyde to phenol may be as low as 0.5 and is preferably in the range 0.8 to 2:1.

We have found that the process of the present invention gives relatively low levels of dialdehyde by-product even when using high molar ratios of formaldehyde to phenol. This is of importance in the manufacture of intermediate for metal extractant compositions, since the presence of dialdehyde in the 2-hydroxyarylaldehyde intermediate gives rise to deleterious impurities in the product.

The reaction is preferably performed in a substantially non-polar anhydrous medium, preferably an aromatic medium. Suitable non-polar liquids are for example benzene, toluene, xylene, mesitylene, cumene, cymene, tetralin, anisole and chlorinated aromatic hydrocarbons such as monochlorobenzene, and orthodichlorobenzene. Toluene and xylene are especially preferred solvents.

The group R in the formula $Sn(OR)_4$ is preferably an aryl or an alkyl group and is conveniently the residue of the phenol involved in the present process, or of methanol, which is a by-product of the present process. The tin compound is conveniently formed by the reaction of for example tin chlorides, oxides, hydroxides, acetylacetonates and nitrates with the phenol or methanol preferably in the presence of an anhydrous alkali. Tin tetrachloride (stannic chloride) is an especially preferred starting material. The reaction conveniently takes place in the solvent that is to be used for the reaction of the formaldehyde and the phenol. Conveniently there is used an excess of the phenol over that required to form the compound Sn(OR)$_4$. If desired the excess of the phenol may correspond to that required to react with the formaldehyde according to the present invention. Suitable alkalis are the hydrides, hydroxides, oxides, alkoxides or phenoxides of the alkali and alkaline earth metals.

The process of the present invention requires that the tin composition is such that, on extraction with 1 to 10 volumes of water, the resultant aqueous medium has a pH of from 6 to 10. It is emphasised that the extraction with water does not form a part of the process of the invention but is a test characterising the tin composition. The test is simply undertaken by removing a portion of the tin composition and shaking with waer. The pH of the resulting aqueous medium may be measured by pH meter or other suitable means. When the tin compound is formed by reaction of a suitable tin starting material with a phenol or methanol in the presence of an alkali, mineral acid produced during the reaction is neutralised by the alkali. It is thus a simple matter to adjust the addition of the tin compound to give the desired pH of the test solution following extraction with water.

Preferably the pH of the aqueous medium following extraction with water is approximately neutral, for example from 6 to 7.5.

The proportions of the tin composition are preferably such that there is present from 1.5 to 5 moles of tin per 100 moles of the (substituted) phenol. Higher proportions of the tin compostion may be used if desired, but give no particular benefit. We have found that if proportions of tin composition lower than 1.5 moles of tin per 100 moles of the phenol are used, the selectivity of the reaction to the desired product may be reduced. A proportion of tin composition such that there is present from about 2 to about 3 moles of tin per 100 moles of the (substituted) phenol is especially preferred.

The tertiary amine may be described by the general formula NR$_1$R$_2$R$_3$, where R$_1$, R$_2$ and R$_3$, which may be the same or different, are preferably alkyl groups. Preferably the total number of carbon atoms contained in the groups R$_1$, R$_2$ and R$_3$ is not greater than 30. Conveniently R$_1$, R$_2$ and R$_3$ are the same and are preferably lower alkyl groups containing from 1 to 3 carbon atoms. We have found that a faster reaction is obtained with such lower alkyl groups than when the tertiary amine contains for example n-octyl groups. The tertiary amine containing lower alkyl groups is also more readily removed from the reaction mixture by conventional means such as distillation.

There is preferably employed from 1 to 20 moles of tertiary amine per mole of tin in the catalyst. We have found that improved selectivity to the desired product (reduced tar formation) is obtained if there is employed more than about 3 moles of amine per mole of tin in the catalyst. The is no particular advantage in employing greater than about 8 moles of amine per mole of tin in the catalyst.

The promotion of the present process by amines is surprising in view of the reported finding that free amines interfere with an inhibit the formylation of phenols and the dehydrogenation of hydroxymethyl phenols using tin phenoxide as catalyst.

The process of the invention is further illustrated by the following Examples and unless otherwise indicated in the Examples all parts and percentages are by weight.

EXAMPLE 1

(a) Present Process

4-Nonylphenol (22 g, 100 millimoles, mmoles) and potassium hydroxide (10 mmoles) were azeotroped until dry (overnight) in toluene (175 ml). On cooling to room temperature stannic chloride (2.5 mmoles) was added such that, on extraction of a portion of the product with water, the pH was 6.5. Commercially available tri-n-octylamine (10 mmoles) was added. The volume of the reaction mixture was made up to 250 ml with dry toluene and the mixture was stirred for 30 minutes under nitrogen. Paraformaldehyde (9 g, 300 mmoles) was then added and the temperature was raised to 100° C. and held for 22 hours. IR analysis of the reaction mixture at the end of this period showed it to contain 67.5 mmoles of 5-nonylsalicylaldehyde and 35 mmoles of unchanged 4-nonylphenol. The amount of dialdehyde was too small to measure accurately by GLC analysis and was less than 2 percent of the product.

Conventional IR techniques are limited in the determination of absolute concentrations such as are required for the calculation of selectivity to the desired product. The major by-product of the reaction determining selectivity is the formation of tars. The level of tar formation was therefore measured by a differential thermal analysis (DTA). It was found that 33% of the solvent-free residue of the reaction (5-nonyl salicylaldehyde, 4-nonylphenol and tars) was involatile.

(b) Comparative Process

The procedure of Example 1(a) was repeated with the omission of the potassium hydroxide to simulate the general reaction conditions employed in the experiments reported in JCS (Perkin I) 1980, p.1862 Table 1. On extraction of a portion of the tin composition with water, the pH was 7.5. IR analysis of the reaction mixture at the end of the 22 hour reaction period indicated the presence of only 17.5 mmoles of 5-nonylsalicylaldehyde and 47.5 mmoles of unconverted 4-nonylphenol. DTA analysis showed that 47.3% of the solvent-free product of the reaction was involatile.

These results demonstrate the much higher yield and selectivity obtained using the process of the present invention as compared to that of the process of the prior art when using an acceptably low level of tin catalyst.

(c) Comparative Process

The procedure of Example 1(a) was repeated but with the omission of the tri-n-octylamine. IR analysis of the reaction mixture at the end of the reaction period showed it to contain 24.5 mmoles of 5-nonylsalicylaldehyde and 31.5 mmoles of unchanged 4-nonylphenol. The lower yield of the desired product is apparent.

EXAMPLE 2

4-Nonylphenol (1100 g, 5.0 moles) and potassium hydroxide (112.2 g, 2.0 moles) were added to toluene (300 g) and azeotroped under nitrogen until dry. On cooling to 124° C., stannic chloride (125.1 g, 0.48 moles) was added over a period of 44 minutes. Fifteen minutes after the addition of the stannic chloride was completed, a 10 ml sample of the solution was removed and extracted with 50 ml of deionised water with shaking.

After allowing the phases to separate, the pH of the aqueous medium was found to be 6.9 as measured by a pH meter. Sixty minutes after the addition of the stannic chloride was completed, a further sample of the solution was removed and, on extraction with water, the pH of the aqueous medium was found to be 7.0, indicating that the formation of the tin composition was complete.

After cooling to 80° C., triethylamine (303 g, 3.0 moles) was added over a period of 6 minutes. The clear red-brown liquid product was cooled and made up to 2 kg of catalyst solution with dry toluene.

Portions of the catalyst solution prepared as above were used for successive preparations of 5-nonylsalicylaldehyde. Thus to 80 g of the catalyst solution was added further nonyl phenol (132 g) and the solution was made up to one litre with further dry toluene (681.2 g). Paraformaldehyde (72 g) was added and the mixture was heated to 98° to 101° C. under a water-cooled condenser and partial take-off head whilst nitrogen was passed through the reaction mixture at a rate of about 80 ml/min. After 6 hours, the sample of the reaction mixture was analysed by high pressure liquid chromatography (HPLC) and found to contain 1.4% unreacted nonyl phenol and 14.6% 5-nonylsalicylaldehyde.

I claim:

1. A process for the preparation of a hydroxyaraldehyde which comprises reacting, in an anhydrous medium, formaldehyde and a phenol free from substituents in the 2-position, in the presence of a catalyst comprising (1) a tertiary amine and (2) a tin composition which is the product of reacting a tin chloride, a tin oxide, a tin hydroxide, a tin acetylacetonate or a tin nitrate with the phenol or methanol in the presence of an anhydrous alkali, wherein the tin composition is such that, on extraction with 1 to 10 volumes of water, the resultant aqueous medium has a pH of 6 to 10.

2. A process according to claim 1 wherein the phenol is a 4-alkylphenol in which the alkyl group contains from 5 to 20 carbon atoms.

3. A process according to claim 1 wherein the formaldehyde is in a polymeric form.

4. A process according to claim 1 wherein the tertiary amine is tri-n-octylamine.

5. A process according to claim 1 wherein the tin composition is prepared from tin tetrachloride and an excess of the phenol in the solvent that is to be used for the reaction of the formaldehyde and the excess of said phenol.

6. A process according to claim 1 wherein the solvent is toluene or xylene.

7. A process according to claim 1 wherein the tertiary amine is an amine of the formula NR1R2R3 wherein R1, R2 and R3 are alkyl groups containing 1 to 3 carbon atoms.

8. The process of claim 1 wherein the alkali is a hydride, hydroxide, oxide, alkoxide or phenoxide of an alkali or alkaline earth metal.

9. The process of claim 1 wherein the tin composition is present in an amount of from 1.5 to 5 moles of tin per 100 moles of the phenol.

* * * * *